United States Patent [19]
Vanmaele

[11] Patent Number: 5,811,554
[45] Date of Patent: Sep. 22, 1998

[54] PREPARATION OF 2-AMINO-4-ALKOXYTHIAZOLES BEING NEGATIVELY SUBSTITUTED IN THE 5 POSITION

[75] Inventor: Luc Vanmaele, Lochristi, Belgium

[73] Assignee: Agfa-Gevaert, N.V., Mortsel, Belgium

[21] Appl. No.: 831,538

[22] Filed: Apr. 8, 1997

Related U.S. Application Data

[62] Division of Ser. No. 428,864, Apr. 25, 1995, abandoned.

[30] Foreign Application Priority Data

Jun. 17, 1994 [EP] European Pat. Off. ........... 94201737.7

[51] Int. Cl.$^6$ .................................................. C07D 277/54
[52] U.S. Cl. ........................................... 548/112; 548/184
[58] Field of Search ...................... 548/184, 112

[56] References Cited

U.S. PATENT DOCUMENTS 4,324,899   4/1982   Frishberg .

FOREIGN PATENT DOCUMENTS 0524401   1/1993   European Pat. Off. .
0578870   1/1994   European Pat. Off. .

*Primary Examiner*—Robert Gerstl
*Attorney, Agent, or Firm*—Baker & Botts, L.L.P.

[57] ABSTRACT

PREPARATION OF 2-AMINO-4-ALKOXYTHIAZOLES BEING NEGATIVELY SUBSTITUTED IN THE 5 POSITION

According to the present invention, 2-amino-4-alkoxythiazoles substituted with an electron withdrawing group in the 5-position are prepared by reacting an iminoether with a halogenating agent and thiourea. Alternatively, the 2-amino-4-alkoxythiazoles are prepared by reacting an iminoether with sodium thiocyanate and an oxidizing agent. According to a further aspect of the invention, novel azo dyes are prepared from such 2-amino-4-alkoxythiazoles having a phosphonyl group in the 5 position.

3 Claims, No Drawings

PREPARATION OF 2-AMINO-4-ALKOXYTHIAZOLES BEING NEGATIVELY SUBSTITUTED IN THE 5 POSITION

This application is a divisional of U.S. patent application Ser. No. 08/428,864, filed Apr. 25, 1995, now abandoned.

FIELD OF THE INVENTION.

This invention belongs to the field of organic chemistry. More particularly, it relates to the preparation of novel substituted 2-amino-4-alkoxythiazoles and azo dyes prepared therefrom.

BACKGROUND OF THE INVENTION

Various synthetic methods are available for preparing 2-amino-4-substituted thiazoles and that are negatively substituted in the 5-position, i.e. that contain an electron withdrawing group in the 5-position. However, 2-amino-4-alkoxy substituted thiazoles with an electron withdrawing substituent in the 5-position cannot be prepared by one of the known methods.

In U.S. Pat. No. 4,324,899 the preparation of 4-substituted thiazoles corresponding to formula (I) is disclosed. This method proceeds according to scheme 1 shown below.

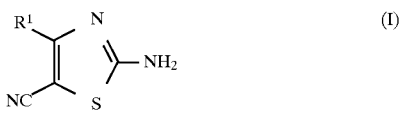

According to U.S. Pat. No. 4,324,899 $R^1$ includes an alkoxy group of 1–20 carbons. However, it appears to be impossible to prepare thiazoles of formula (I), with $R^1$=alkoxy, according to scheme 1 because, when R1=alkoxy, compound A obtained after step 1 is 2-amino-4-hydroxythiazole ($R^1$=OH), also called pseudothiohydantoin.

This has been shown by M. Robba and R. C. Moreau (Ann. Pharm. Franc., 22, 14 (1964)), by C. F .H. Allen and J. A. Vanallen (Crg. Syn., 27, 71-73 (1947)), and in the Chemistry of Heterocyclic Compounds, Thiazole and its Derivatives, Part One, edited by J. V. Metzger (Wiley and Sons, 1979).

Scheme 1

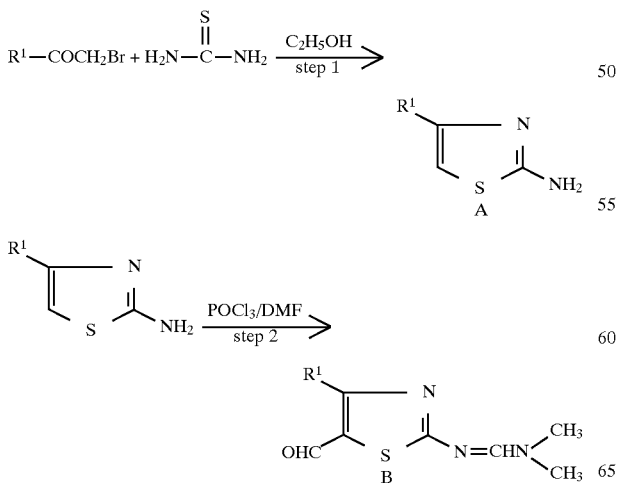

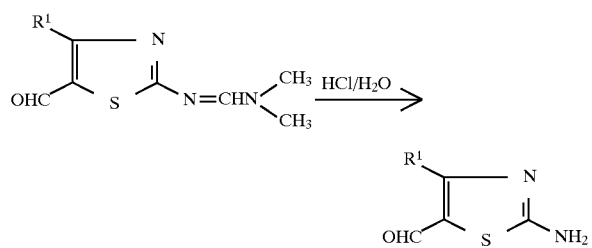

Moreover, it is known that treatment of compound A ($R^1$OH) with $POCl_3$/DMF as mentioned in U.S. Pat. No. 4,324,899, yields compound B with $R^1$=Cl instead of $R^1$=hydroxy or alkoxy. This has been disclosed by R. Egli in U.S. Pat. No. 4,395,544.

In EP 0,524,401 the preparation of thiazole azo dyes is described. The preparation is based upon the diazotation of compounds of formula (II).

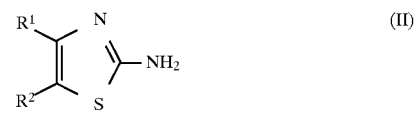

One of the substituents selected for $R^1$ is a $C_1$-$C_4$-alkoxy group and for $R^2$ cyano, formyl, etc. can be selected. In EP 0 524 401 the preparation of compounds of formula (II) is not disclosed but reference is made to Houben-Weyl, Methoden der Organischen Chemie, Band 10/3, DE-A-3,015,121, DE-A-2,329,388, DE-A-2,851,514, EP-A-139,444, DE-A-2,713,573, DE-A-3,412,293 or US-A-4,324,899.

However, from these references it is known that 2-amino-4-alkoxy -thiazoles, negatively substituted at the 5-position, cannot be prepared according to the synthetic procedures mentioned. The references cited in EP 0,524,401 demonstrate that the synthetic procedures described are not applicable for the preparation of 2-amino -4-alkoxy-thiazoles negatively substituted at the 5-position.

From the prior art it is thus clear that there is no synthetic method available for the synthesis of 2-amino-4-alkoxy thiazoles that are negatively substituted at the 5-position.

It is very desirable to have a synthetic method for the synthesis of 2-amino-4-alkoxy-thiazoles that are negatively substituted at the 5-position, because these compounds are important intermediates in the synthesis of dyes, especially azo dyes, and pharmaceutically active compounds.

SUMMARY OF THE INVENTION

The present invention provides a new, efficient synthetic method for the preparation of various novel 2-amino-4-alkoxy-thiazoles negatively substituted at the 5-position, which are useful as intermediates in the synthesis of dyes, especially azo dyes, plant protection agents and pharmaceutically active compounds.

These intermediates can for example be diazotized and coupled with azo components such as anilines, pyrazolones, pyridones, phenoles, naphtholes, acetoacetanilides, etc.

DETAILED DESCRIPTION OF THE INVENTION

The present invention provides compounds of general formula (III):

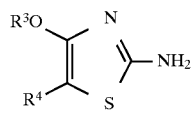

(III)

wherein :

R⁴ represents cyano, $$\begin{matrix} O \\ \parallel \\ C-R^5, \end{matrix}$$

SO$_2$R$^6$, POR$^7$R$^8$;

R$^3$ represents alkyl, alkenyl, aryl, alkynyl, or a heterocyclic group;

R$^5$ represents hydrogen, SR$^9$, OR$^9$, NR$^{10}$R$^{11}$;

R$^6$ represents alkyl, alkenyl, aryl, alkynyl, or a heterocyclic group, OR$^9$ or NR$^{10}$R$^{11}$;

R$^7$ and R$^8$ each independently represent alkyl, alkenyl, aryl, alkyloxy, aryloxy, alkylthio, arylthio, an amino group, a heterocyclic group or R$^7$ and R$^8$ together with the atoms to which they are attached represent the necessary atoms to form a 5- or 6-membered ring;

R$^9$ represents hydrogen, alkyl, alkenyl, aryl, alkynyl, or a heterocyclic group;

R$^{10}$ and R$^{11}$ each independently represent hydrogen, alkyl, alkenyl, aryl, aralkyl, a heterocyclic group or R$^{10}$ and R$^{11}$ together with the atoms to which they are attached represent the necessary atoms to form a 5- or 6-membered ring.

The compounds according to the present invention can be prepared in high yields and in a one-pot reaction according to scheme 2. Two procedures of general utility for preparing these types of compounds can be used.

The first one comprises the reaction in a solvent of a readily available iminoether according to formula (IV) or the hydrochloride or other salt thereof and a halogenating agent. As a solvent there is preferably used an alcohol such as methanol, ethanol, propanol, isopropanol, butanol, sec. butanol, tert. butanol, 2-methylpropanol, pentanol, etc.. The reaction is preferably carried out at from about −25° C. to about 70° C. more preferably from about −10° C. to about 50° C., and for an adequate time, for example, for about 1–120 minutes, preferably for about 1–45 minutes. As a halogenating agent there is preferably used N-chlorosuccinimide, N-bromosuccinimide or 1,3-dibromo-5,5-dimethylhydantoin. The reaction is preferably carried out in the presence of a base, such as an amine, if the salt of the iminoether is used.

The halogenating agent may be dissolved in any solvent or mixture of solvents, such as dipolar aprotic solvents, e.g. N-methylpyrrolidone, dimethylacetamid, halogenated solvents such as dichloromethane or inert solvents such as hexane, toluene, ethylacetate. Alternatively, the halogenating agent can be added as as a solid.

Any suitable molar ratio can be used, but a molar ratio of from about 1:1 to about 2:1 of the iminoether to the halogenating agent is preferred. If desired, from about 0.5 to 2 moles of base, preferably from about 0.9 to 1.5 moles of base, may be used.

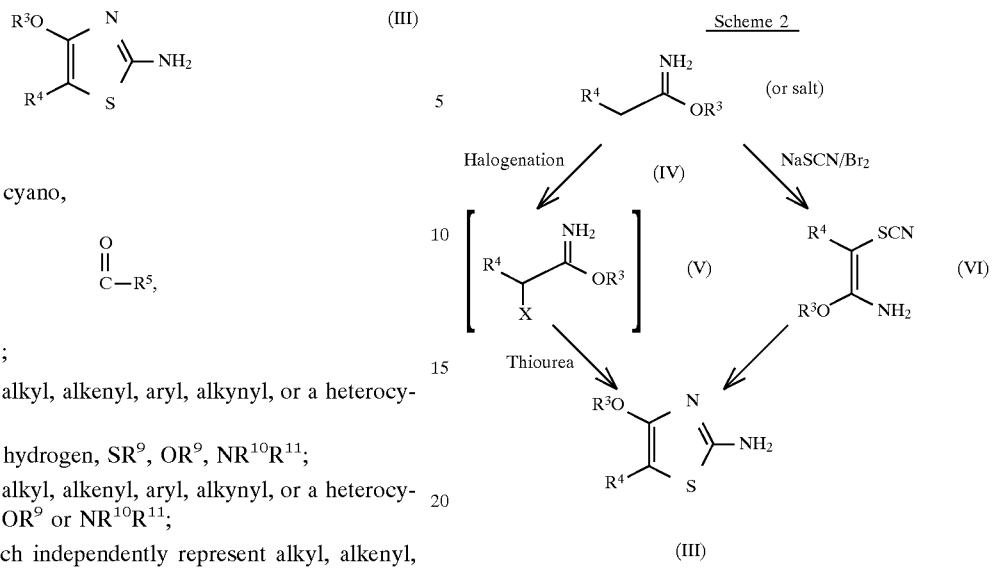

In the above scheme R$^3$ and R$^4$ have the same meaning as defined before and X represents a halogen.

The intermediate of formula (V) is then treated with thiourea. Suitable amounts of thiourea are from about 0.5 to 2 moles, preferably from about 0.8 to 1.4 moles. The reaction is preferably carried out at from about 40° C. to about 250° C., preferably at reflux temperature, for about 1 minute to 10 hours, preferably for about 5 minutes to 60 minutes. Thiourea may be dissolved in any solvent or mixture of solvents, such as dipolar aprotic solvents, halogenated solvents, or inert solvents. Water is preferably kept to a minimum to prevent hydrolysis of the iminoether or salt thereof. Alternatively, thiourea can be added as as a solid. Iminoethers according to formula (IV) can easily be prepared according to literature procedures, such as Methoden der Organischen Chemie (Houben-Weyl), Band 5, Carbonsäuren und Carbonsäurederivative, Teil 1; a preferred method is the Pinner synthesis.

The second method comprises the reaction in a solvent of a readily available iminoether according to formula (IV) or the hydrochloride or other salt thereof and a thiocyanate, e.g. sodium thiocyanate, with a solution of an oxidant, preferably bromine, in a solvent, preferably acetic acid or an inert solvent. The solvent for the reaction is preferably an alcohol, such as methanol, ethanol, propanol, isopropanol, etc., or an acid such as acetic acid. The reaction is preferably carried out at from about −25° C. to about 70° C., preferably from about −15° C. to about 25° C., and for an adequate time, for example, for about 1–300 minutes, preferably for about 1–60 minutes. Any suitable molar ratio between the iminoether and the thiocyanate can be used, but a molar ratio of from about 1:1 to about 1:4, preferably from about 1:1 to about 1:2, of the iminoether to thiocyanate can be used. A molar ratio of from about 1:1 to 1:2, preferably 1:1, of the iminoether to the oxidant can be used. The oxidant is used to generate thiocyanogen in the reaction mixture. Intermediate (VI) can also be prepared using thiocyanogen directly.

The intermediates of formula (VI) are then transformed into compounds of formula (III) by heating the reaction mixture at from about 40° C. to about 250° C., preferably at reflux temperature, for about 1 minute to 10 hours, preferably for about 1–4 hours. Intermediates of formula (VI) can be isolated.

The preparation of compounds according to formula (III) is described into more detail in the experimental section, without the intention of limiting the scope thereto.

Compounds of formula (III) are especially useful as the diazo moiety of azo dyes prepared through diazotization and coupling with azo components (Z) according to scheme 3.

Scheme 3

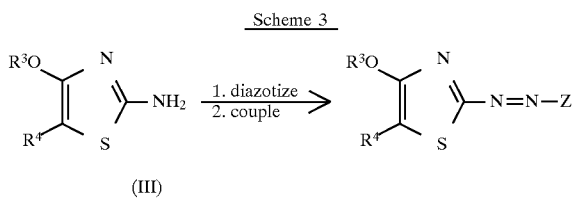

Especially preferred are those compounds wherein Z is selected from anilines, pyrazolones, phenols, naphtholes, pyridones, acetoacetanilides, 1,2,3,4-tetrahydroquinolines, 2,3-dihydroindoles and 3,4-dihydro-2H-1,4-benzoxazines. As a further aspect of the present invention there are provided novel dyes of formula (VII)

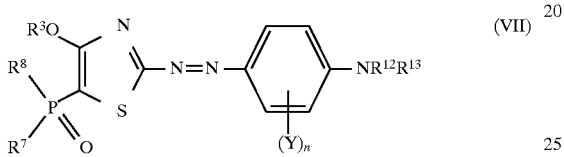

wherein $R^3$, $R^7$, $R^8$ have the same meaning as described before;

Y represents any substituent, e.g. SH, OH, $NH_2$, halogen, CN, $NO_2$, alkyl, carbonamido, sulphonamido, acylamino, sulphonylamino, alkoxy, thioalkoxy;

n represents 0, 1, 2, 3 or 4, the Y substituents being the same or different when n is greater than 1, or the Y substituents can form a fused-on ring system;

$R^{12}$ and $R^{13}$ each independently represent hydrogen, alkyl, aryl, or $R^{12}$ and $R^{13}$ together with the atoms to which they are attached represent the atoms necessary for completing a heterocyclic ring, or $R^{12}$ and/or $R^{13}$ together with Y represent the atoms necessary for completing a fused-on heterocyclic ring.

Resentative examples of compounds according to general (III) and formula (VII) are given in table 1 and table 2 further illustrating the invention.

TABLE 1

| Compound | $R^4$ | $R^3$ |
|---|---|---|
| 1 | CN | $CH_3$ |
| 2 | CN | $C_2H_5$ |
| 3 | CN | $C_3H_7$ |
| 4 | CN | $C_4H_9$ |
| 5 | CN | $CH(CH_3)C_2H_5$ |
| 6 | CN | $CH_2CH(CH_3)_2$ |
| 7 | CN | $C_6H_5$ |
| 8 | CN | F1 |

TABLE 1-continued

| Compound | $R^4$ | $R^3$ |
|---|---|---|
| 9 | CN | F2 |
| 10 | CN | $CH_2CH=CH_2$ |
| 11 | CN | $CH(CH_3)_2$ |
| 12 | CN | $C(CH_3)_3$ |
| 13 | CN | $C_6H_{13}$ |
| 14 | CN | $CH_2C_6H_5$ |
| 15 | CN | $CH_2CH_2C_6H_5$ |
| 16 | CN | F3 |
| 17 | CN | $CH_2-C\equiv CH$ |
| 18 | CN | F4 |
| 19 | CHO | $CH_3$ |
| 20 | CHO | $C_2H_5$ |
| 21 | CHO | $C_3H_7$ |
| 22 | CHO | $C_4H_9$ |
| 23 | CHO | $CH(CH_3)C_2H_5$ |
| 24 | CHO | $CH_2CH(CH_3)_2$ |
| 25 | CHO | $CH_2CH=CH_2$ |
| 26 | CHO | F1 |
| 27 | $CO_2C_2H_5$ | $C_2H_5$ |
| 28 | $CO_2CH_3$ | $CH_3$ |
| 29 | $CONHCH_3$ | $CH_3$ |
| 30 | $CONHCH_3$ | $C_2H_5$ |
| 31 | $CON(C_2H_5)_2$ | $CH_3$ |
| 32 | $CON(C_2H_5)_2$ | $C_2H_5$ |
| 33 | $PO(OC_2H_5)_2$ | $C_2H_5$ |
| 34 | $PO(OC_2H_5)_2$ | $CH_3$ |
| 35 | $PO(OCH_3)_2$ | $CH_3$ |
| 36 | $PO(OCH_3)_2$ | $C_2H_5$ |
| 37 | $SO_2OCH_3$ | $CH_3$ |
| 38 | $SO_2OCH_3$ | $C_2H_5$ |
| 39 | COOH | $CH_3$ |
| 40 | COOH | $C_2H_5$ |

In the above the table, the symbols F1, F2, F3 and F4 represent the following fragments (* denotes the linking position).

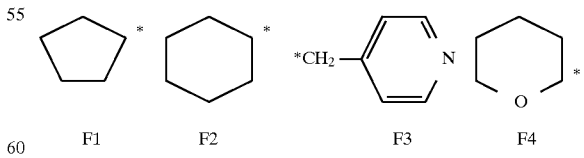

F1  F2  F3  F4

TABLE 2

Structure:
R³O—C(=N)—(S)—C(R⁸)=C—N=N—[phenyl ring with positions 1,2,3]—NR¹²R¹³, with (Y)ₙ on ring at position 3; phosphonate P(=O)(R⁷)(R⁸-substitution on vinyl).

| Dye | $R^{12}$ | $R^{13}$ | $R^3$ | $R^7$ | $R^8$ | n | Y |
|---|---|---|---|---|---|---|---|
| D1 | $C_2H_5$ | $C_2H_5$ | $C_2H_5$ | $OC_2H_5$ | $OC_2H_5$ | 0 | — |
| D2 | $C_4H_9$ | $C_4H_9$ | $C_2H_5$ | $OC_2H_5$ | $OC_2H_5$ | 0 | — |
| D3 | $C_4H_9$ | $CH(CH_3)C_2H_5$ | $C_2H_5$ | $OC_2H_5$ | $OC_2H_5$ | 0 | — |
| D4 | $C_4H_9$ | $CH_2CH(CH_3)_2$ | $C_2H_5$ | $OC_2H_5$ | $OC_2H_5$ | 0 | — |
| D5 | $C_2H_5$ | $C_2H_5$ | $CH_3$ | $OCH_3$ | $OCH_3$ | 0 | — |
| D6 | $C_2H_5$ | $C_2H_5$ | $CH_3$ | $-OCH_2CH_2O-$ | | 0 | — |
| D7 | $C_4H_9$ | $C_4H_9$ | $C_2H_5$ | $OC_2H_5$ | $OC_2H_5$ | 1 | 2-$CH_3$ |
| D8 | $C_4H_9$ | $C_4H_9$ | $C_2H_5$ | $OC_2H_5$ | $OC_2H_5$ | 1 | 2-$OCH_3$ |
| D9 | $C_4H_9$ | $C_4H_9$ | $C_2H_5$ | $OC_2H_5$ | $OC_2H_5$ | 1 | 2-$NHCOCH_3$ |
| D10 | $C_4H_9$ | $C_4H_9$ | $C_2H_5$ | $OC_2H_5$ | $OC_2H_5$ | 2 | 1-$OCH_3$; 3-$NHCOCH_3$ |
| D11 | $C_2H_5$ | $C_2H_5$ | $C_2H_5$ | $CH_3NCH_2$ | $CH_2NCH_3$ | 0 | — |
| D12 | $C_2H_5$ | $C_2H_5$ | $C_4H_9$ | $OC_2H_5$ | $OC_2H_5$ | 0 | — |

D13: diethyl phosphonate-thiazolyl azo dye with 4-morpholinophenyl group.

D14: diethyl phosphonate-thiazolyl azo dye coupled to a julolidine (tetrahydroquinoline-fused) moiety.

D15: diethyl phosphonate-thiazolyl azo dye coupled to N-methyl-1,2,3,4-tetrahydroquinoline.

D16: diethyl phosphonate-thiazolyl azo dye coupled to 4-[N-ethyl-N-(2-methanesulfonamidoethyl)amino]phenyl.

D17: diethyl phosphonate-thiazolyl azo dye coupled to 4-[N-ethyl-N-(2-sulfoethyl)amino]phenyl ($SO_3H$).

EXPERIMENTAL SECTION

The following examples illustrate the preparation of compounds corresponding to general formula (III).

EXAMPLE 1

Preparation of 2-amino-4-methoxy-5-cyanothiazole (compound 1)

Compound 1 is prepared according to scheme 4 (method 1 or method 2). Compound S1 is prepared according to the literature procedures mentioned before.

Scheme 4

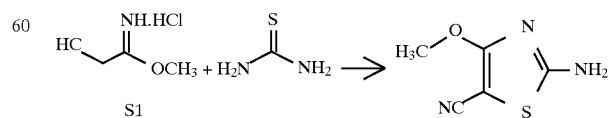

Compound 1

Method 1

A suspension of 88 g of compound S1 in 650 ml of methanol is cooled to 10° C. 91.2 ml of triethylamine are added and the solution is cooled to -50° C. A solution of 93.5 g of 1,3-dibromo-5,5-dimethylhydantoin (DDH) in 100 ml of N,N-dimethylacetamid is added at once and stirring is continued for 3 minutes. 49.4 g of thiourea are added and the reaction mixture is refluxed for 30 minutes. After cooling the reaction mixture is poured. into 3.5 l of water and stirring is continued for 30 minutes. The precipitate is filtered and washed with water. After drying 76 g of compound 1 are obtained (75%). Compound 1 can be crystallised from butyl acetate (melting point : 191° C.). The structure of compound 1 is confirmed by $^1$H-NMR analysis (d$_6$-DMSO (2.5 ppm); 20° C.; 300 MHz) : 3.91 ppm (CH$_3$); 8.33 ppm (NH$_2$) and by $^{13}$C-NMR analysis (d$_6$-DMSO (39.7 ppm); 20° C.) 57.7; 61.3; 114.4; 169.0; 169.6 ppm.

Method 2

21 ml of triethylamine are added to a suspension of 21 g of compound S1 in 200 ml of dichlorciethane at 15° C. 27.8 g of N-bromosuccinimide are added portionwise and stirring is continued for 5 minutes. The reaction mixture is filtered and the solvent is removed under reduced pressure. 100 ml of methanol are added and 11.9 g thiourea are added slowly. The mixture is refluxed for 30 minutes and poured into 500 ml of ice-water. The precipitate is filtered and dried to obtain 15 g of compound 1.

EXAMPLE 2

Preparation of 2-amino-4-ethoxy-thiazole-5-yl-carboxylic acid ethyl ester (compound 28)

Compound 28 is prepared according to scheme 5. Compound S2 is prepared according to the literature procedures mentioned before. Compound 28 is also prepared according to method 1 or method 2 from example 1; starting from compound S2 compound 28 is prepared in ethanol with a yield of more than 70%.

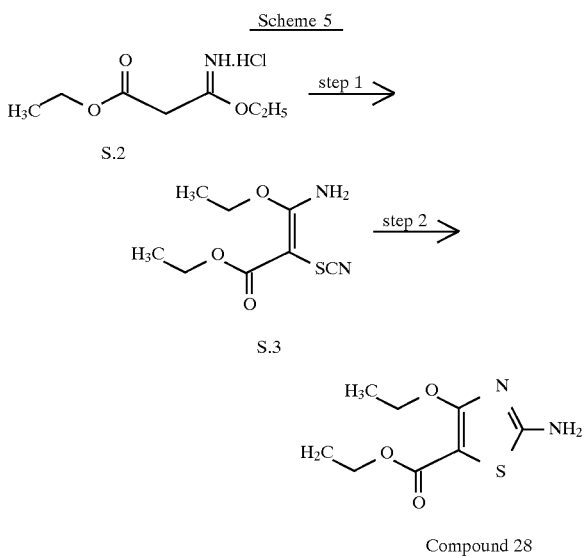

Step 1

A solution of 20 g of compound S2 in 100 ml of ethanol is cooled to 15° C. 13.5 ml of triethylamine and 8.9 g of sodium thiocyanate are added while stirring. The mixture is cooled to −5° C. and a solution of 16.2 g of bromine in 7.5 ml of acetic acid is added slowly. Stirring is continued for 15 minutes at 0° C. The reaction mixture is poured into a solution of 32 g of sodium carbonate in 300 ml of water and 100 g of ice. Stirring is continued for 5 minutes. The precipitate is filtered, washed with water and dried to obtain 16.5 g (75%) of compound S3 (melting point : 106° C.).

Step 2

42 g of compound S3 are dissolved in 200 ml of ethanol and 20 ml of acetic acid. The solution is refluxed for 2.5 hours and cooled at 0° C. while stirring. The precipitate is filtered and washed with ethanol. After drying 29.5 g (70%) of compound 28 are obtained. Compound 28 can be crystallized from acetonitrile to obtain extremely pure product (melting point : 173° C.).

The structure of compound 28 is confirmed by $^1$H-NMR analysis (d$_6$-DMSO (2.5 ppm); 20° C.; 300 MHz) : 1.18 ppm (CH$_3$); 1.27 ppm (CH$_3$); 4.07 ppm (CH$_2$); 4.28 ppm (CH$_2$); 8.00 ppm (NH$_2$) and by $^{13}$C-NMR analysis (d$_6$-DMSO (39.7 ppm); 20° C.) : 14.38; 14.80; 58.75; 65.36; 84.97; 160.64; 164.2; 168.9 ppm.

The structure of compound S3 is confirmed by $^1$H-NMR analysis (d$_6$-DMSO (2.5 ppm); 20° C.; 300 MHz) : 1.21 ppm (CH$_3$); 1.34 ppm (CH$_3$); 4.12 ppm (CH$_2$); 4.28 ppm (CH$_2$); 8.55 and 9.30 ppm (NH$_2$) and by $^{13}$C-NMR analysis (d$_6$-DMSO (39.7 ppm); 20° C.) : 14.0; 14.4; 58.4; 59.5; 65.3; 114.2; 168.4; 169.3 ppm.

Example 3

Preparation of 2-amino-4-ethoxy-thiazole-5-yl-phosphoric acid diethyl ester (compound 34)

Compound 34 is prepared according to scheme 6. Compound S4 is prepared according to the literature procedures mentioned before.

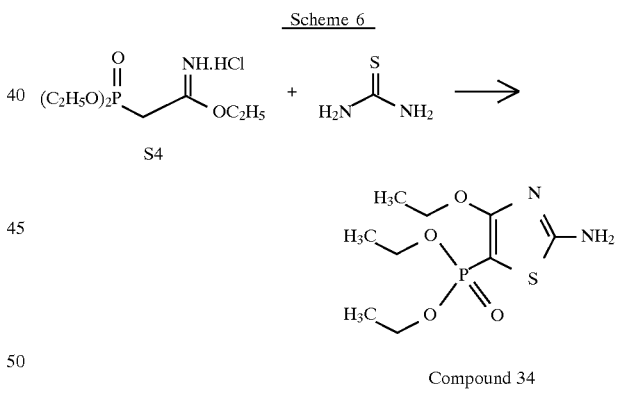

Compound 34

35 g of compound S4 are dissolved in 100 ml of ethanol. 20 ml of triethylamine are added at −5° C. At −5 ° C. 19.3 g of 1,3-dibromo-5,5-dimethylhydantoin (DDH) are added portionwise during a period of 15 minutes. The solution is stirred for 15 minutes at 0° C., followed by the addition of 10.3 g of thiourea. The solution is refluxed for one hour, followed by removal of the solvent under reduced pressure. The residual oil is purified by column chromatography (dichloromethane/ethanol; 95/5) to obtain 4.5 g of pure compound 34 and 1.8 g of compound S7. Compound 34 is crystallized from ethyl acetate/hexane (melting point 117° C.). The structure of compound 34 is confirmed by $^1$H-NMR analysis (d$_6$-DMSO(2.5 ppm); 20° C.; 300 MHZ)=3.88, 3.93 ppm (CH$_2$); 1.22 ppm (CH$_3$); 4.22 ppm (CH$_2$); 1.19 ppm (CH$_3$); 7.79 ppm (NH$_2$); by $^{13}$P-NMR analysis (H$_3$PO$_4$=0.00 ppm (external)=12.97 ppm; and by $^{13}$C-NMR analysis (d$_6$DMSO (39.4 ppm); 20° C.)=170.75 ppm ($^3$J(C,P)=16.0 Hz); 164.26 ppm ($^2$J(C,P)=7.5 Hz); 75.33 ppm ($^1$J(C,P)= 220.4 Hz); 61.10 ppm ($^2$J(C,P)=5.2 Hz); 16.00 ppm ($^3$J(C, P)=6.8 Hz); 65.24 ppm; 14.80 ppm.

Compound S7 (melting point 114° C.) is also confirmed by $^1$H-NMR analysis (d$_6$ –DMSO (2.5 ppm); 20° C; 200 MHz) : 3.83, 3.91 ppm (CH$_2$); 1.20 ppm (CH$_3$); 5.98 ppm (NH$_2$); 7.53 ppm (NH$_2$); by $^{31}$P-NMR analysis (H$_3$PO$_4$= 0.00 ppm (external)=19.14 ppm, and by $^{13}$C-NMR analysis (d$_6$-DMSO (39.4 ppm); 20° C.)=171.57 ppm ($^3$J(C,P)=15.8 Hz); 165.00 ppm ($^2$J(C,P)=13.9 Hz); 65.30 ($^1$J(C,P) =220 Hz); 60.70 ppm ($^2$J(C,P)=4.6 Hz); 16.00 ppm ($^3$J(C,P)=6.6 Hz).

Compound S7 can also be used as an intermediate in the synthesis of dyes, especially azo dyes, plant protection agents and pharmaceutically active compounds.

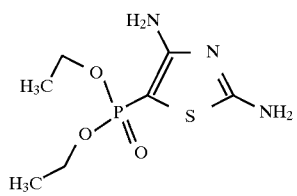

Compound S.7

EXAMPLE 4

Diazotization and coupling. Synthesis of compound S5.

Compound S5 is prepared according to scheme 7.

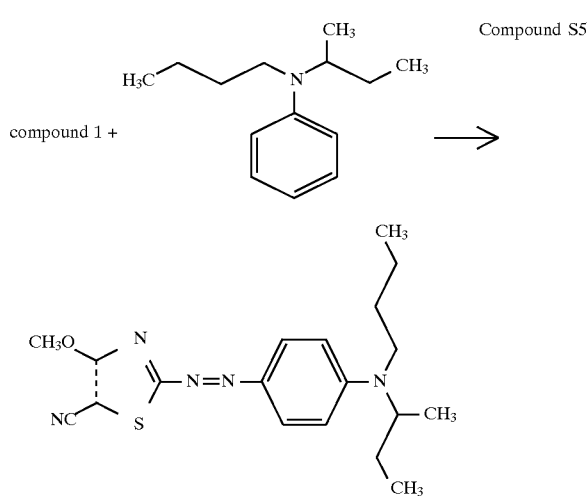

A solution of 10 g of compound 1 in 70 g of phosphoric acid is cooled to −18° C. 12.5 ml of nitrosyl sulphuric acid is added over one hour while maintaining the temperature below −10° C. Stirring is continued for another hour (solution 1).

16 g of N-butyl, N-sec.butylaniline is mixed with 50 g of ice and 30 ml of ethyl acetate (solution 2).

Solution 1 is added slowly to solution 2 and stirring is continued for one hour at room temperature. The precipitate is filtered, washed with water and dried to obtain 11.5 g of compound S5. The dye is purified by column chromatography (dichloromethane/hexane from 1/1 to 7/3) to obtain 8.1 g of pure dye (λmax (CH$_3$OH)=562 nm; $\epsilon_{max}$=51643). The structure is confirmed by $^1$H-NMR analysis.

Example 5

Diazotization and coupling. Synthesis of compound S6.

Compound S6 is prepared according to scheme 8.

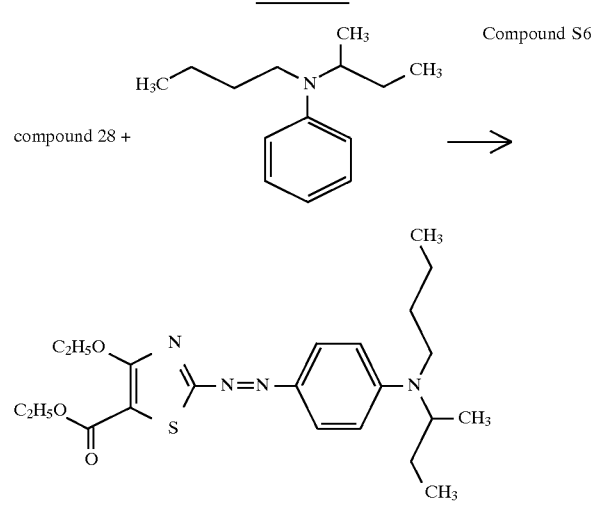

15g of compound 28 are dissolved in a mixture of 120 g of phosphoric acid and 30 g of sulphuric acid at room temperature. The solution is cooled to −10° C. to −15° C. 15.5 ml of nitrosyl sulphuric acid are added slowly at −15° C. and stirring is continued for 20 minutes (solution 1).

15 g of N-butyl, N-sec.butylaniline are mixed with 500 g of ices 200 ml of water and 10 ml of sulphuric acid (solution 2).

Solution 1 is added slowly to solution 2 while stirring. Stirring is continued for 30 minutes. Compound S6 is extracted from the reaction mixture with ethyl acetate and after work-up the dye is purified by column chromatography to obtain 3.2 g of pure dye S6 as an oil (λmax (CH$_3$OH)=552 nm; $\epsilon_{max}$=60192). The structure is confirmed by $^1$H-NMR analysis.

EXAMPLE 6

Preparation of a dye according to formula (VII). Preparation of compound D3.

Compound D3 is prepared according to scheme 9.

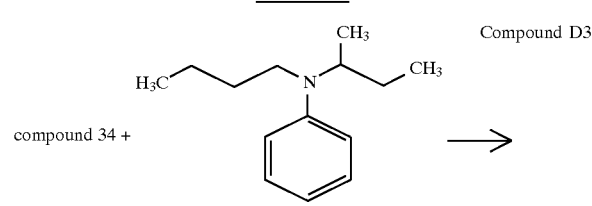

-continued
Scheme 9

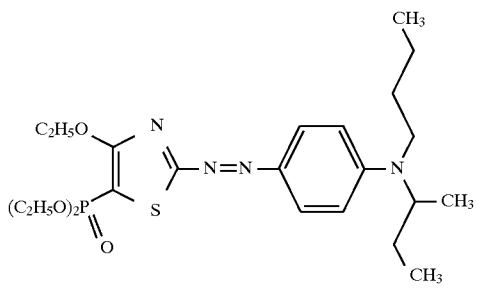

1.4g of compound 34 are suspended in 14 ml of phosphoric acid at room temperature. 1.1 ml of nitrosyl sulphuric acid are added at −10° C. and stirring is continued at −5° C. (solution 1). 1.2 g of N-butyl, N-sec. butylaniline are mixed with 20 ml of ethyl acetate and 100 g of ice (solution 2). Solution 1 is added slowly to solution 2 while stirring. Stirring is continued for 30 minutes. 25 g of sodium acetate, 300 ml of water and 50 ml of ethyl acetate are added. The organic layer is separated, washed with water, dried and concentrated under reduced pressure to obtain 1.98 g of oil which is further purified by column chromatrography to obtain 1 g of pure compound D3 as an oil ($\lambda$max(CH$_2$Cl2) =538nm; $\epsilon_{max}$=43555).

The structure of compound d3 is confirmed by $^{31}$P-NMR analysis (H$_3$PO$_4$ =0.00 ppm (external)) : 11.40 ppm and by $^1$H-NMR analysis (d$_6$-DMSO(2.5 ppm); 20° C.; 300 MHz); 7.90, 6.77 (fenyl); 3.25, 3.33 (N-CH$_2$); 1.60 (CH$_2$); 1.40 (CH$_2$); 0.98(CH$_3$); 4.03(N-CH); 1.40, 1.70(CH$_2$); 0.93 (CH$_3$); 1.27(CH$_3$); 4.60(CH$_2$—O); 1.43(CH$_3$); 4.13, 4.21 (CH$_2$—O—P=O); 1.37(CH$_3$)

I claim:

1. A process for the production of a compound according to the following general formula (III):

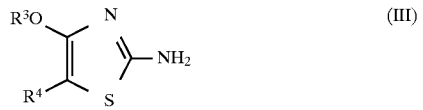

(III)

wherein:

$R^4$ represents cyano,

$SO_2R^6$, $POR^7R^8$;

$R^3$ represents alkyl, alkenyl, aryl, alkynyl, or a heterocyclic group;

$R^5$ represents hydrogen, $SR^9$, $OR^9$, $NR^{10}R^{11}$;

$R^6$ represents alkyl, alkenyl, aryl, alkynyl, or a heterocyclic group, $OR^9$ or $NR^{10}R^{11}$;

$R^7$ and $R^8$ each independently represent alkyl, alkenyl, aryl, alkyloxy, aryloxy, alkylthio, arylthio, an amino group, a heterocyclic group or $R^7$ and $R^8$ together with the atoms to which they are attached represent the necessary atoms to form a 5- or 6- membered ring;

$R^9$ represents hydrogen, alkyl, alkenyl, aryl, alkynyl, or a heterocyclic group; $R^{10}$ and $R^{11}$ each independently represent hydrogen, alkyl, alkenyl, aryl, aralkyl, a heterocyclic group or $R^{10}$ and $R^{11}$ together with the atoms to which they are attached represent the necessary atoms to form a 5- or 6-membered ring, comprising reacting an iminoether according to the following formula

IV wherein $R^3$ and $R^4$ have the same meaning as defined above or a salt of said iminoether, with a halogenating agent and thiourea.

2. A process according to claim 2 wherein the compound of formula III is selected from the group consisting of:

2-amino-4-methoxy-5-cyano-thiazole;

2-amino-4-ethoxy-5-cyano-thiazole;

2-amino-4-ethoxy-thiazole-5-yl-carboxylic acid ethyl ester;

2-amino-4-methoxy-thiazole-5-yl-carboxylic acid methyl ester;

2-amino-4-methoxy-5-formyl-thiazole;

2-amino-4-ethoxy-5-formyl-thiazole;

2-amino-4-ethoxy-thiazole-5-yl-phosphonic acid diethyl ester and 2-amino-4-methoxy-thiazole-5-yl-phosphonic acid dimethyl ester.

3. A process according to claim 2 wherein the halogenating agent is selected from the group consisting of N-chlorosuccinimide, N-bromosuccinimide and 1,3-dibromo-5,5-dimethylhydantoin.

* * * * *